(12) United States Patent
Desai et al.

(10) Patent No.: US 9,511,078 B2
(45) Date of Patent: Dec. 6, 2016

(54) SELF-NANOEMULSION OF POORLY SOLUBLE DRUGS

(71) Applicant: Kashiv Pharma, LLC, Bridgewater, NJ (US)

(72) Inventors: Dipen Desai, Whippany, NJ (US); Siva Ram Kiran Vaka, Piscataway, NJ (US); Navnit H. Shah, Clifton, NJ (US); Anekant Jain, Allentown, PA (US); Wantanee Phuapradit, Montville, NJ (US)

(73) Assignee: Kashiv Pharma, LLC, Bridgewater, NJ (US)

( * ) Notice: Subject to any disclaimer, the term of this patent is extended or adjusted under 35 U.S.C. 154(b) by 0 days.

(21) Appl. No.: 14/899,801

(22) PCT Filed: Jun. 19, 2014

(86) PCT No.: PCT/US2014/043198
§ 371 (c)(1),
(2) Date: Dec. 18, 2015

(87) PCT Pub. No.: WO2014/205226
PCT Pub. Date: Dec. 24, 2014

(65) Prior Publication Data
US 2016/0151392 A1    Jun. 2, 2016

Related U.S. Application Data

(60) Provisional application No. 61/836,836, filed on Jun. 19, 2013.

(51) Int. Cl.
*A61K 31/58* (2006.01)
*A61K 31/57* (2006.01)
*A61K 31/216* (2006.01)
*A61K 9/107* (2006.01)

(52) U.S. Cl.
CPC ............. *A61K 31/58* (2013.01); *A61K 9/1075* (2013.01); *A61K 31/216* (2013.01); *A61K 31/57* (2013.01)

(58) Field of Classification Search
CPC ...... A61K 31/58; A61K 31/57; A61K 31/216; A61K 9/1075
See application file for complete search history.

(56) References Cited

FOREIGN PATENT DOCUMENTS

WO    2010150144 A2    12/2010

OTHER PUBLICATIONS

C . J . H. Porter et al., "Lipids and lipid-based formulations: optimizing the oral delivery of lipophilic drugs," Nature Reviews Drug Discovery, vol. 6, pp. 231-248, 2007.
C. M. Hansen in Hansen Solubility Parameters : A User's Handbook, 2nd Ed., CRC Press , Boca Raton, Florida , 2007.
C. W. Pouton et al., "Formulation of lipid-based delivery systems for oral administration: Materials , methods and strategies,"Advanced Drug Delivery Reviews, vol. 60, pp. 625- 637, 2008.
Charman SA et al: "Self-emulsifying drug delivery systems: Formulation and biopharmaceutic evaluation of an Investigational lipophilic compound", Pharmaceutical Research 1992 US, vol. 9, No . 1, 1992, pp. 87-93, KP002730377.
D. W. Van Krevelen and P. J . Hoftyzer, "Properties of Polymers", 2nd Ed., Elsevier , New York, 1976, Chapter 7, pp. 129-159.
International Search Report for Application No. PCT/US2014/043198 dated Nov. 21, 2014.
J . Hildebrand and R. L. Scott, "Solubility of Nonelectrolytes", 3rd Ed., Reinhold, New York, 1950, Chapter 23, pp. 424-439.
Ming Sun et al: "Design, preparation and in vitro evaluation of paclitaxel-loaded self-nanoemulsifying drug delivery system", Asian Journal of Pharmaceutical Sciences, Jan. 1, 2011, pp. 18-25, XP055143182, Retrieved from the Internet: <http://www.asianjps.com:8080/fileup/PDF/AJPS2011,6(1)-3.pdf> [retrieved on Sep. 29, 2014].
Partial International Search Report for Application No. PCT/US2014/043198 dated Oct. 10, 2014.

*Primary Examiner* — Trevor Love
(74) *Attorney, Agent, or Firm* — Lerner, David, Littenberg, Krumholz & Mentlik, LLP

(57) ABSTRACT

The present disclosure pertains to pharmaceutical formulation comprising low aqueous solubility drug, a solubilizer, and optionally at least one pharmaceutically acceptable excipient that form dispersions when exposed to an aqueous environment.

11 Claims, No Drawings

SELF-NANOEMULSION OF POORLY SOLUBLE DRUGS

CROSS-REFERENCE TO RELATED APPLICATIONS

The present application is a national phase entry under 35 U.S.C. §371 of International Application No. PCT/US2014/043198 filed Jun. 19, 2014, published in English, which claims priority from U.S. Provisional Patent Application No. 61/836,836 filed Jun. 19, 2013, all of which incorporated herein by reference.

INTRODUCTION

The present disclosure relates to the field of drug-containing formulations, and more particularly to nonaqueous formulations that form dispersions when combined with aqueous fluids.

The Biopharmaceutics Classification System ("BCS") has been developed to describe drug substances by their aqueous solubility and intestinal permeability properties:

Class I—high permeability, high solubility drugs that are well absorbed.

Class II—high permeability, low solubility drugs having bioavailability that is limited by the solubilization rate.

Class III—low permeability, high solubility drugs having bioavailability that is limited by the permeation rate.

Class IV—low permeability, low solubility drugs having poor bioavailability and high variability of pharmacokinetics parameters (e.g., AUC and $C_{max}$).

A drug is considered to be highly soluble under the BCS when its highest unit dosage strength is soluble in 250 mL or less of aqueous media over the pH range of 1 to 7.5. Many drug substances, however, fall within Classes II and IV. Formulating dosage forms to deliver such drugs, particularly when large amounts of the drugs must be delivered in each dose, is very challenging. The absolute drug solubility is not always the most important parameter, since residence times in various sites within the gastrointestinal system after oral administration vary, and it is usually necessary to have a drug in solution during its transit through the particular sites where it can be systemically absorbed. Examples of drugs having low aqueous solubility are those that form solutions with water having concentrations no greater than 1 mg/mL, or no greater than 0.1 mg/mL.

A large number of useful drug substances have poor solubility in water, which complicates their successful administration by the oral route. Fluids in the gastrointestinal tract are aqueous and orally administered drugs that do not have adequate solubility can exhibit poor systemic absorption as they pass through the gastrointestinal tract. In many instances, only a small fraction of the quantity of a drug in a unit dosage form will actually be absorbed into the circulatory system, the remaining drug simply passing through the digestive tract and being excreted. This is not desirable, since many drug substances are rather expensive. In addition, extra quantities of contained drug usually increase the physical sizes of dosage forms, rendering them more difficult to swallow. Certain individuals can be capable of absorbing a greater or lesser fraction of the available drug, depending on particular conditions in their bodies and/or whether the dosage form was ingested under fed or fasted conditions, and this contributes to undesired therapeutic variability.

Various approaches for improving the solubility properties of drugs have been tried. Sometimes, different polymorphic forms, including crystalline, solvated, and amorphous forms, will have different solubilities and a suitable form can be chosen to meet a specific requirement. For many substances, solubility can be enhanced by reducing the particle sizes; an increased particle surface area generally results in a more rapid dissolution rate. However, these approaches are not without difficulties, since very small particles generally have poor flow and handling properties that can affect drug content uniformity in a formulation, and many polymorphic forms do not have sufficient physical stability to undergo formulation processing and the subsequent storage over a typical product shelf life, without converting to a different form.

Administering a drug in a dissolved form can assist with overcoming solubility limitations. However, many drugs need to be protected from acidic conditions in the stomach, so the oral administration of solutions can be disfavored.

Certain oral pharmaceutical products have been developed in solid forms containing a drug dissolved in a nonaqueous solvent material, together with an emulsifying agent. Such dosage forms can form dispersions of drug-containing droplets upon entering an aqueous environment. The drug frequently is intended to remain within the droplets during passage through the stomach, so it will be relatively unaffected by acid and gastric enzymes. Ultimately, the droplets might decompose in a higher-pH environment, such as the duodenum or intestines. If a digestible oil, such as a vegetable oil, is used as the solvent, the droplets might be decomposed by a normal digestion process involving lipase and other agents. However, the digestion process is subject to high rate variability, and this factor does not favor such formulations.

These nonaqueous formulations are deemed "self-emulsifying" and can be classified based on the particle sizes that will form upon entry into an aqueous environment, as self-emulsifying drug delivery systems ("SEDDs") producing particle sizes substantially less than 1 µm, self-microemulsifying drug delivery systems ("SMEDDS") with smaller particles, and self-nanoemulsifying drug delivery systems ("SNEDDS") with the smallest particles. The scientific basis for this type of drug delivery is explained by C. J. H. Porter et al., "Lipids and lipid-based formulations: optimizing the oral delivery of lipophilic drugs," *Nature Reviews Drug Discovery*, Vol. 6, pages 231-248, 2007. A number of useful components for these formulations have been described in the literature, such as the article by C. W. Pouton et al., "Formulation of lipid-based delivery systems for oral administration: Materials, methods and strategies," *Advanced Drug Delivery Reviews*, Vol. 60, pages 625-637, 2008, and these authors note the poor understanding of drug stability in lipid vehicles, as well as other aspects of the formulations that are problematic.

Abiraterone is a drug that is used to treat prostate cancer, and has a chemical name (3β)-17-(3-pyridinyl)androsta-5,16-dien-3-ol. A product containing abiraterone acetate as the active ingredient is being marketed as ZYTIGA® tablets. ZYTIGA® doses must be taken with an empty stomach (i.e., no food for at least two hours before and one hour after dosing), since food causes a substantial enhancement of drug systemic absorption that is highly variable and not predictable. Abiraterone $C_{max}$ and $AUC_{0-\infty}$ values were approximately 7- and 5-fold higher, respectively, when ZYTIGA® was administered with a low-fat meal (7% fat, 300 calories) and approximately 17- and 10-fold higher, respectively, when abiraterone acetate was administered with a high-fat meal (57% fat, 825 calories). This type of restriction on food intake adversely affects patient compliance with prescribed therapy. In addition, the usual one gram daily dose is an inconvenient four tablets containing 250 mg of the drug, taken at once, and drug bioavailability is low.

The drug progesterone is a steroid hormone that is involved in the female reproductive cycle. It has a chemical name pregn-4-ene-3,20-dione and is the active ingredient in PROMETRIUM® capsules containing 100 and 200 mg of the drug, prescribed in conjunction with conjugated estrogens for treating endometrial hyperplasia in non-hysterectomized postmenopausal women. The drug also is used for treating secondary amenorrhea. PROMETRIUM® capsules contain the drug in a micronized form to enhance its solubility, suspended in peanut oil. Progesterone is metabolized primarily by the liver, largely to form pregnanediols and pregnanolones, which further limits bioavailability. Absolute bioavailability of the drug is unknown, but is thought to be low.

Fenofibrate is a lipid regulating drug and has a chemical name 2-[4-(4-chlorobenzoyl)phenoxy]-2-methyl-propanoic acid, 1-methylethyl ester. It is being marketed as Fenofibrate tablets, containing 54 mg or 160 mg of fenofibrate. The absorption of fenofibrate is increased when administered with food. With fenofibrate tablets, the extent of absorption is increased by approximately 35% under fed as compared to fasting conditions. Hence, food intake adversely affects patient compliance with prescribed therapy.

Improvements in formulations to deliver low-solubility drugs, such as abriaterone, progesterone, and fenofibrate, are needed to reduce food effects and high pharmacokinetic variability, which can improve overall safety and patient compliance with therapy.

SUMMARY OF THE INVENTION

The present invention is directed to a pharmaceutical formulation containing a low aqueous solubility drug, a solubilizer, an emulsifier, and optionally at least one additional pharmaceutically acceptable excipient, formulated in a capsule and therapeutic uses thereof. The low aqueous solubility drug is solubilized within the other components of the pharmaceutical formulation which forms a nanoemulsion upon exposure to an aqueous environment, such as the gastrointestinal tract, where a mean particle size (D50) of a droplet of the emulsion in the aqueous environment typically ranges from about 50 nm to about 800 nm.

Without wishing to be bound by any particular theory of operation, it is believed that a nanoemulsion-forming formulation eliminates the need for the dissolution of active pharmaceutical ingredient particles in the gastrointestinal tract. As the active pharmaceutical ingredient is already in solution form when it is administered, the formulation thereby maximizes bioavailability and minimizes pharmacokinetic variability induced by concomitant food intake. Therefore, it is believed that the formulation can be administered without regard to meals, thus improving safety and patient compliance. It is also believed that the nanoemulsion-forming formulation may overcome first-pass metabolism because the low aqueous solubility active pharmaceutical ingredient is incorporated in an oil phase of the resulting emulsion and delivered via the intestinal lymphatic route, which may circumvent the liver and thereby restrain the hepatic first pass metabolism.

DETAILED DESCRIPTION

One aspect of the present invention is directed to a pharmaceutical formulation comprising a low aqueous solubility drug, a solubilizer, an emulsifier, and optionally at least one pharmaceutically acceptable excipient. Thus, in some embodiments, an excipient, such as an antioxidant and/or a co-solvent, is included. In some embodiments, the low aqueous solubility drug is present in a dissolved state. In some embodiments, pharmaceutical formulation is substantially free of water. Some embodiments comprise trace amounts of water from impurities that may be present in certain formulation components.

The terms such as "about", "up to", "generally", "substantially" and the like are to be construed as modifying a term or value such that it is not an absolute. Such terms will be defined by the circumstances and the terms that they modify as those terms are understood by those of skill in the art. This includes, at very least, the degree of expected experimental error, technical error and instrumental error for a given experiment, technique or an instrument used to measure a value. The term "about" is used to provide flexibility to a numerical range endpoint by providing that a given value may be "a little above" or "a little below" the endpoint. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum.

As used herein, "substantially free of" a particular compound or excipient means that there is less than 5% w/w of a particular compound or excipient, wherein the amount present does not impart any functional value to the formulation.

As used herein, an "effective amount" or a "therapeutically effective amount" of a drug refers to a non-toxic, but sufficient amount of the drug, to achieve a therapeutic effect in treating a condition for which the drug is known to be effective.

The terms "drug", "active agent", "active pharmaceutical ingredient (API)," and "pharmaceutically active agent" are used interchangeably herein to refer to a chemical compound that induces a desired pharmacological and/or physiological effect. The terms also encompass pharmaceutically acceptable derivatives of those active agents specifically mentioned herein, including, but not limited to, salts, esters, solvates, hydrates, complexes with one or more molecules, pro-drugs, active metabolites, lipophilic derivatives, analogs, and the like.

The term "low aqueous solubility drug" as used herein, refers to an active pharmaceutical agent which has an aqueous solubility of less than 2% by weight, which can be determined using standard testing methods, such as the rotating disc method.

The term "pharmaceutically acceptable salts" as used herein, includes those salts which are within the scope of sound medical judgment and suitable for use in contact with the tissues of humans and lower animals without undue toxicity, irritation, allergic response and the like. They are well known in the art. The salts can be prepared in situ during the final isolation and purification of the compounds of the invention, or separately by reacting the pharmaceutically active substance having a free base function with a suitable organic acid or inorganic acid.

As used herein, the term "solid dosage form" generally refers to a pharmaceutical formulation which, when used in an oral mode of administration is in the form of a capsule, tablet, pill, powder or granule. In such solid dosage forms, the active compound is mixed with at least one inert, pharmaceutically acceptable excipient or carrier.

As used herein the term "low molecular weight polyethylene glycols" (PEGs) refers to a polyethylene glycol with a molecular weight of less than about 1,000 g/mol.

As used herein the term "treating" includes prophylaxis of a physical and/or mental condition or amelioration, mitigation, or elimination of the developed condition once it has been established or alleviation of the characteristic symptoms of such condition.

As used herein, the term "ambient temperature" is defined as a temperature ranging from about 18° C. to about 25° C.

As used herein the terms "self-emulsifying" or "auto-emulsifying" pharmaceutical formulation is defined as a formulation that spontaneously forms an emulsion when introduced into an aqueous phase.

Embodiments of the pharmaceutical formulation comprise a therapeutically effective amount of a low aqueous solubility active pharmaceutical ingredient. In some embodiments, the low aqueous solubility active pharmaceutical ingredient includes abiraterone, progesterone, or fenofibrate. In some embodiments, abiraterone is present in amounts ranging from about 1 mg to about 1000 mg. In further embodiments, abiraterone is present in amounts ranging from about 5 mg to about 500 mg. In still further embodiments, abiraterone is present in amounts ranging from about 10 mg to about 250 mg.

In some embodiments, progesterone is present in amounts ranging from about 1 mg to about 500 mg. In further embodiments, progesterone is present in amounts ranging from about 5 mg to about 250 mg. In still further embodiments, progesterone is present in amounts ranging from about 10 mg to about 200 mg.

In some embodiments, fenofibrate is present in amounts ranging from about 1 mg to about 500 mg. In further embodiments, fenofibrate is present in amounts ranging from about 5 mg to about 250 mg. In still further embodiments, fenofibrate is present in amounts ranging from about 10 mg to about 250 mg.

The pharmaceutical formulation comprises a solubilizer. Representative examples of solubilizers that may be useful in the practice of the present invention include monoesters of glycerin having fatty acid groups comprising about 8 to about 12 carbon atoms, monoesters of propylene glycol having fatty acid groups comprising about 8 to about 12 carbon atoms, and combinations thereof. In some embodiments, a solubilizer has self-emulsifying properties and has hydrophilic/lipophilic balance (HLB) values of about 3 to about 7. In some embodiments, the solubilizer comprises glyceryl monocaprylate, glyceryl monocaprate, glyceryl monolaurate, propylene glycol monocaprylate, glyceryl monocaprylate/monocaprate, propylene glycol monolaurate, including medium chain fatty acids (i.e., Caprylic acid, Capric acid, Lauric acid), or combinations thereof. In some embodiments, the amount of the solubilizer used is sufficient to maintain the particular drug in solution, and will depend upon the solubility parameters of individual drug and solubilizers. In some embodiments, the solubilizer is present in an amount of about 5% to about 95% by weight of the formulation. In further embodiments, the solubilizer is present in an amount of about 10% to about 90% by weight of the formulation. In still further embodiments, the solubilizer is present in an amount of about 25% to about 85% by weight of the formulation.

The "solubility parameter" concept is useful for predicting the ability of solutes and solvents to form solutions. This is based on a concept proposed by J. Hildebrand and R. L. Scott, *Solubility of Nonelectrolytes*, $3^{rd}$ Ed., Reinhold, N.Y., 1950, that is based on the vaporization enthalpy of substances. Modifications to the original calculation method have been made, including the equation described by C. M. Hansen in *Hansen Solubility Parameters: A User's Handbook*, $2^{nd}$ Ed., CRC Press, Boca Raton, Fla., 2007. A modification to the method was made by D. W. Van Krevelen and P. J. Hoftyzer in *Properties of Polymers*, $2^{nd}$ Ed., Elsevier, New York, 1976 to separately estimate the dispersion component, the polar component, and the hydrogen bonding component of cohesive forces, and tables of the various components for many substances are given in the literature. Solubility parameters are expressed in the pressure units $(MPa)^{1/2}$.

The solubility of drug compounds also can be indicated by their partition coefficients, determined by measuring equilibrium concentrations of an unionized compound (obtained, if necessary, by adjusting the pH of an aqueous phase) in the phases of immiscible aqueous and organic liquids. In some embodiments, the immiscible aqueous liquid is water and the organic liquid is octanol. A partition coefficient value for this system is calculated by the equation:

log $P$=log(concentration in octanol÷concentration in water).

Without wishing to be bound by any particular theory, it has been found that solubility parameter values of abiraterone acetate, progesterone, and fenofibrate generally correspond to the values of certain solubilizers, thereby maximizing the drug miscibility and solubility. Also, it is believed that drug compounds having log P values of 3-7 exhibit good solubility in solubilizers having HLB values of 3-7. Examples of the parameters are given in the table below.

| Drug | Calculated Solubility Parameter* | Log P |
|---|---|---|
| Progesterone | 19.44 | 3.5 |
| Abiraterone acetate | 22.78 | 5.12 |
| Fenofibrate | 22.67 | 5.24 |

| Solubilizer | Calculated Solubility Parameter* | HLB Value |
|---|---|---|
| Propylene glycol monocaprylate | 20.15 | 6.0 |
| Glyceryl monocaprylate | 24.15 | 4.7 |

*Calculated by the Van Krevelen and Hoftyzer equation.

In general, drug solubility will be optimized if the difference in solubility parameters between the drug substance and the solubilizer is less than about 2, 3, 4, or 5, or in embodiments is less than about 6 or about 7. Smaller differences between solubility parameter values of the drug and solubilizer will facilitate miscibility of the drug and solubilizer, maximizing the drug solubility.

The pharmaceutical formulation comprises an emulsifier. In some embodiments, the emulsifier is nonionic, anionic, cationic, or amphoteric. Representative examples of emulsifiers that may be useful in the practice of the present invention include polyethoxylated oils, such as polyoxyl castor oils (e.g., PEG-40 hydrogenated castor oil, polyoxyl 35 castor oil, etc.), polysorbates such as polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), and polysorbate 80 (polyoxyethylene (20) sorbitan monooleate), and sorbitan esters of fatty acids such as sorbitan monolaurate, sorbitan monopalmitate, sorbitan monostearate, and sorbitan monooleate. Combinations of any two or more emulsifiers are useful. In some embodiments, the emulsifier is present in an amount of about 1% to about 50% by weight of the formulation. In further embodiments, the emulsifier is present in an amount of about 5% to about 50% by weight of the formulation.

In some instances, the pharmaceutical formulation may crystallize at room temperature or at higher temperatures. In order to inhibit or prevent such crystallization, the formulation may include a crystallization inhibitor. Crystallization renders the emulsion unstable and has an adverse effect on shelf life. Useful crystallization inhibitors include polymers, such as polyvinylpyrrolidones and cellulose ethers that are soluble in the solubilizer. In some embodiments, the crystallization inhibitor is a hydroxypropyl cellulose, such as the commercial product KLUCEL® EF, or a povidone in grades such as K12, K17, and K30, or combinations thereof. In some embodiments, the crystallization inhibitor is present in an amount from about 0.1% to about 10% by weight of the formulation. In further embodiments, the crystallization inhibitor is present in an amount from about 1.0% to about 10% by weight of the formulation. In still further embodiments, the crystallization inhibitor is present in an amount from about 1.0% to about 5% by weight of the formulation.

In some embodiments, the pharmaceutical formulation comprises an antioxidant, which may assist with maintaining drug stability in the formulation. Useful antioxidants include tocopherols, butylated hydroxyanisole, butylated hydroxytoluene, etc., including combinations of any two or more thereof. When present, the antioxidant is present in an amount of about 0.01% to about 1.0% by weight of the formulation. In some embodiments, the antioxidant is present in an amount of about 0.01% to about 0.5% by weight of the formulation. In further embodiments, the antioxidant is present in an amount of 0.05% to 0.1% by weight of the formulation.

In some embodiments, the pharmaceutical formulation comprises an chelating agent. Oxidation that is promoted by the presence of transition metal ions. An example of a chelating agent is ethylenediaminetetraacetic acid or a salt thereof, which may be used with or without another antioxidant component. When present, the chelating agent is present in an amount of about 0.01% to about 1.0% by weight of the formulation. In some embodiments, the chelating agent is present in an amount of about 0.01% to about 0.5% by weight of the formulation. In further embodiments, the chelating agent is present in an amount of 0.05% to 0.1% by weight of the formulation.

In some embodiments, a co-solvent ingredient for the drug is also present. Useful co-solvents include propylene glycol, low molecular weight polyethylene glycols (e.g., PEG 400), triacetin, triethyl citrate, ethanol, glycofurol, etc. In some embodiments, the co-solvent is present in an amount of 0.1% to 20% by weight of the formulation. In further embodiments, the co-solvent is present in an amount of 1.0% to 20% by weight of the formulation. In still further embodiments, the co-solvent is present in an amount of 5.0% to 10% by weight of the formulation.

The formulations may be prepared using simple low-shear mixing processes. For example, in embodiments a solubilizer (e.g., propylene glycol monocaprylate, glyceryl monocaprylate, etc.) is heated using a jacketed vessel and controlled at temperatures of about 50-55° C. An antioxidant is added for the purpose of removing potential free radicals that may be present in the solubilizer, promoting long-term stability of the formulated product. The drug and a crystallization inhibitor (e.g., a low viscosity grade of hydroxypropyl cellulose such as KLUCEL® EF) are added to the mixture of solubilizer and antioxidant while mixing at about 50-55° C. to obtain solubilization of the drug. An emulsifier (e.g., polyoxyl 35 castor oil) is added to the drug solution with mixing at about 50-55° C. until a clear solution is obtained. The final solution is cooled to ambient temperature and can then be encapsulated into dosage forms having a desired drug content.

Formulations can be contained in soft capsules, such as those made from gelatin, or two-piece hard capsules, such as those made from gelatin, starches, hydroxypropyl methylcelluloses, or other substances. As capsules, the formulations of the invention are usually packed into a hard shell composed of two pieces fitted together or a soft, one-piece, closed shell, which may vary in shape and size. Hard and soft capsules consist mainly of gelatin. Soft gelatin capsules are particularly suitable for formulations with a semisolid consistency and, if required, also viscous liquid consistency.

After a swallowed capsule containing a formulation is ingested, the contained formulation will mix with gastric fluids and stomach contractions can assist in forming a nanoemulsion.

The particle size distribution of the nanoemulsion can be determined using standard techniques such as optical microscopy, electrical impedance measurement (i.e., the Coulter Principle), and laser light diffraction. Suitable diffraction instruments include those from Malvern Instruments Ltd., Malvern, Worcestershire, United Kingdom, and from HORIBA Instruments Inc., Irvine, Calif. USA. Results from instrumental methods may be expressed as "D" values such as D10, D50, D90, and D95, where the numeric portion is the percentage of particles having sizes less than or equal to a specified value. For example, a result D50=100 nm indicates that about 50% of the particles have sizes not exceeding about 100 nm.

In general, the nanoemulsions that are produced when the pharmaceutical formulation is mixed with an aqueous fluid have dispersed droplet with mean "particle" sizes (D50) no greater than 500 nm, 400 nm, 300 nm, 200 nm, 100 nm, or 50 nm. A nanoemulsion is formed when the formulation is exposed to gastrointestinal fluids and provides rapid and uniform drug dissolution, improving the bioavailability of the contained drug. In addition, the formulations will reduce inter- and intra-subject pharmacokinetic variability and reduce or eliminate the food effect, while increasing systemic exposure of the contained poorly soluble drugs.

Another aspect of the present invention is directed to a method of treating prostate cancer comprising administering to a patient in need thereof, a pharmaceutical formulation comprising abiraterone; a solubilizer; and an emulsifier. In some embodiments, abiraterone is present in amounts ranging from about 1 mg to about 1000 mg. In further embodiments, abiraterone is present in amounts ranging from about 5 mg to about 500 mg. In still further embodiments, abiraterone is present in amounts ranging from about 10 mg to about 250 mg.

In another embodiment, is a method of treating amenorrhea comprising administering to a patient in need thereof, a pharmaceutical formulation comprising progesterone; a solubilizer; and an emulsifier. In some embodiments, progesterone is present in amounts ranging from about 1 mg to about 500 mg. In further embodiments, progesterone is present in amounts ranging from about 5 mg to about 250 mg. In still further embodiments, progesterone is present in amounts ranging from about 10 mg to about 200 mg.

In another embodiment, is a method of treating endometriosis comprising administering to a patient in need thereof, a pharmaceutical formulation comprising progesterone; a solubilizer; and an emulsifier. In some embodiments, progesterone is present in amounts ranging from about 1 mg to about 500 mg. In further embodiments, progesterone is present in amounts ranging from about 5 mg to about 250 mg. In still further embodiments, progesterone is present in amounts ranging from about 10 mg to about 200 mg.

In another embodiment, is a method of treating adenomyosis comprising administering to a patient in need thereof, a pharmaceutical formulation comprising progesterone; a solubilizer; and an emulsifier. In some embodiments, progesterone is present in amounts ranging from about 1 mg to about 500 mg. In further embodiments, progesterone is present in amounts ranging from about 5 mg to about 250 mg. In still further embodiments, progesterone is present in amounts ranging from about 10 mg to about 200 mg.

In another embodiment, is a method of treating endometrial hyperplasia comprising administering to a patient in need thereof, a pharmaceutical formulation comprising progesterone; a solubilizer; and an emulsion. In some embodiments, progesterone is present in amounts ranging from about 1 mg to about 500 mg. In further embodiments, progesterone is present in amounts ranging from about 5 mg to about 250 mg. In still further embodiments, progesterone is present in amounts ranging from about 10 mg to about 200 mg.

In another embodiment, is a method of regulating blood lipid levels comprising administering to a patient in need thereof, a pharmaceutical formulation comprising fenofibrate; a solubilizer; and an emulsifier. In some embodiments, fenofibrate is present in amounts ranging from about 1 mg to about 500 mg. In further embodiments, fenofibrate is present in amounts ranging from about 5 mg to about 250 mg. In still further embodiments, fenofibrate is present in amounts ranging from about 10 mg to about 250 mg.

In another embodiment, is a method of treating high blood cholesterol levels comprising administering to a patient in need thereof, a pharmaceutical formulation comprising fenofibrate; a solubilizer; and an emulsifier. In some embodiments, fenofibrate is present in amounts ranging from about 1 mg to about 500 mg. In further embodiments, fenofibrate is present in amounts ranging from about 5 mg to about 250 mg. In still further embodiments, fenofibrate is present in amounts ranging from about 10 mg to about 250 mg.

The following examples are provided solely for the purpose of illustrating certain specific aspects and embodiments, and should not be considered as limiting the scope of this disclosure in any manner.

EXAMPLE 1

Formulations 1A-1D are prepared, using the ingredients in the table below.

| | mg/Capsule | | | |
|---|---|---|---|---|
| Ingredient | 1A | 1B | 1C | 1D |
| Abiraterone acetate (API) | 150 | 120 | 100 | 80 |
| dl-α-Tocopherol (antioxidant) | 0.5 | 0.5 | 0.5 | 0.5 |

-continued

| | mg/Capsule | | | |
|---|---|---|---|---|
| Ingredient | 1A | 1B | 1C | 1D |
| Hydroxypropyl cellulose* (crystallization inhibitor) | 16 | 16 | 16 | 16 |
| Polyoxyl 35 castor oil† (emulsifier) | — | 100 | 150 | 200 |
| Propylene glycol monocaprylate‡ (solubilizer) | q.s. to 800 | | | |

*e.g., KLUCEL ® EF, a product of Ashland.
†e.g., KOLLIPHOR ® EL, a product of BASF.
‡e.g., CAPMUL ® PG-8, a product of Abitec Corp.

Manufacturing Procedure:

1. Propylene glycol monocaprylate is heated to 50±5° C. and dl-α-tocopherol is added with mixing to form a solution, followed by sequentially adding and dissolving hydroxypropyl cellulose and abiraterone acetate. Polyoxyl 35 castor oil, if required, is then added and dissolved.

2. The solution is cooled to ambient temperature and filled into soft gelatin, hard gelatin, or hard hydroxypropyl methylcellulose capsules.

EXAMPLE 2

Formulations 2A-2C are prepared, using the ingredients in the table below.

| | Weight Percent | | |
|---|---|---|---|
| Ingredient | 2A | 2B | 2C |
| Progesterone (API) | 6 | 6 | 6 |
| Triethyl citrate (co-solvent) | 10 | — | 10 |
| Polyoxyl 35 castor oil (emulsifier) | 30 | 35 | 40 |
| Hydroxypropyl cellulose* (crystallization inhibitor) | 1 | 1 | — |
| dl-α-Tocopherol (antioxidant) | 0.05 | 0.05 | — |
| Propylene glycol monocaprylate (solubilizer) | q.s. to 100 | | |

*e.g., KLUCEL ® EF, a product of Ashland

Manufacturing Procedure:

1. Combine dl-α-tocopherol (if required) and propylene glycol monocaprylate at 55-60° C., then sequentially add polyoxyl 35 castor oil and the required quantity of triethyl citrate, with continuous mixing at that temperature.

2. Gradually add the required quantity of hydroxypropyl cellulose with mixing at 55-60° C. Continue mixing at that temperature, until hydroxypropyl cellulose dissolves.

3. Add progesterone and mix at 55-60° C. until a clear solution is obtained. Continue mixing for another 30 minutes after the progesterone is completely dissolved at 55-60° C., then cool the solution to ambient temperature and mix for an additional 30 minutes.

4. Fill a desired quantity into soft gelatin, hard gelatin, or hard hydroxypropyl methylcellulose capsules.

The formulations are tested for various properties, as follows:

Heat Stability: Heat the formulation to 60° C. and maintain for 30 minutes under stirring, then cool to ambient temperature and maintain the stirring for 30 minutes. There should be no drug precipitation or separation of phases during the test.

Sonication Stability: Sonicate the formulation for 30 minutes, and there should be no visible phase changes.

Aqueous Dilution: Add an amount of the formulation equivalent to 50 mg of progesterone to 250 mL of simulated gastric fluid and stir slowly for 10-15 minutes. There should not be any visible phase separation and the formed dispersion should be transparent to translucent.

Particle Size: The dispersion is maintained under continuous stirring and particle size distribution is measured using a Malvern Mastersizer 2000.

Storage Stability: The formulation should not exhibit visible phase separation after two weeks of storage, cycling the formulation between 60° C. and 5° C. every 2-3 days.

Results of the testing are shown in the following table.

|  | Formulation | | |
|---|---|---|---|
| Test | 2A | 2B | 2C |
| Heat Stability | Maintained as solution | | |
| Sonication Stability | | | |
| Aqueous Dilution | Nanoemulsion formed | | |
| Particle Size | D85 = 100 nm | D95 = 100 nm | D90 = 200 nm |
| Storage Stability | Maintained as solution | | |

EXAMPLE 3

A formulation is prepared, using the ingredients in the table below.

| Ingredient | Weight Percent |
|---|---|
| Abiraterone acetate (API) | 10 |
| Propylene glycol monocaprylate (solubilizer) | 61.56 |
| PEG-40 hydrogenated castor oil* (emulsifier) | 26.38 |
| Hydroxypropyl cellulose (crystallization inhibitor) | 2 |
| dl-α-Tocopherol (antioxidant) | 0.06 |

*e.g., KOLLIPHOR ® RH40, a product of BASF.

Manufacturing Procedure:

1. At 55-60° C., propylene glycol monocaprylate and dl-α-tocopherol are combined, hydroxypropyl cellulose is slowly added with stirring until a solution is formed, abiraterone acetate is added and dissolved, and finally PEG-40 hydrogenated castor oil is added and mixed well. Stirring of the solution is continued for 30 minutes after it has cooled to ambient temperature.

2. Quantities containing a desired amount of abiraterone acetate are encapsulated into soft gelatin, hard gelatin, or hard hydroxypropyl methylcellulose capsules.

The formulation is tested for various properties, as follows:

Heat Stability: Heat the formulation to 60° C. and maintain for 30 minutes under stirring, then cool to ambient temperature and maintain the stirring for 30 minutes. There should be no drug precipitation or separation of phases during the test.

Sonication Stability: Sonicate the formulation for 30 minutes, and there should be no visible phase changes.

Aqueous Dilution: Add an amount of the formulation equivalent to 60 mg of abitaterone acetate to 250 mL of simulated gastric fluid and stir slowly for 10-15 minutes. There should not be any visible phase separation and the formed dispersion should be transparent to translucent.

Particle Size: The dispersion (1-2 drops of the formulation in 160 mL of simulated gastric fluid (SGF)) is maintained under continuous stirring and particle size distribution is measured using a Malvern Mastersizer 2000 by Mie theory.

Storage Stability: The formulation should not exhibit visible phase separation after two weeks of storage, cycling the formulation between 60° C. and 5° C. every 2-3 days.

Results of the testing are shown in the following table.

| Test | Result |
|---|---|
| Heat Stability | Maintained as solution |
| Sonication Stability | |
| Aqueous Dilution | Nanoemulsion formed |
| Particle Size | D10 = 80 nm |
| | D50 = 186 nm |
| | D90 = 377 nm |
| Storage Stability | Maintained as solution |

EXAMPLE 4

Formulations 4A, 4B are prepared, using the ingredients in the table below.

| | Weight Percent | |
|---|---|---|
| Ingredient | 4A | 4B |
| Fenofibrate (API) | 6 | 6 |
| Glyceryl caprylate (solubilizer) | 80.05 | 80.05 |
| Polyoxyl castor oil* (emulsifier) | 8.9 | 8.9 |
| Hydroxypropyl cellulose** (crystallization inhibitor) | 5 | — |
| Povidone K30LP (crystallization inhibitor) | — | 5 |
| dl-α-Tocopherol (antioxidant) | 0.05 | 0.05 |

*e.g., KOLLIPHOR ® EL, a product of BASF
**e.g., KLUCEL ® EF, a product of Ashland Manufacturing Procedure:

1. At 55-60° C., Glyceryl caprylate and dl-α-tocopherol are combined, hydroxypropyl cellulose/Povidone K30LP is slowly added with stirring until a solution is formed, fenofibrate is added and dissolved, and finally Polyoxyl castor oil is added and mixed well. Stirring of the solution is continued for 30 minutes after it has cooled to ambient temperature.

2. Quantities containing a desired amount of fenofibrate, are encapsulated into soft gelatin, hard gelatin, or hard hydroxypropyl methylcellulose capsules.

The formulation is tested for various properties, as follows:

Heat Stability: Heat the formulation to 60° C. and maintain for 30 minutes under stirring, then cool to ambient temperature and maintain the stirring for 30 minutes. There should be no drug precipitation or separation of phases during the test.

Sonication Stability: Sonicate the formulation for 30 minutes, and there should be no visible phase changes.

Aqueous Dilution: Add an amount of the formulation equivalent to 30 mg of fenofibrate to 250 mL of simulated gastric fluid and stir slowly for 10-15 minutes. There should not be any visible phase separation and the formed dispersion should be transparent to translucent.

Particle Size: The dispersion (1-2 drops of the formulation in 160 mL of SGF) is maintained under continuous stirring and particle size distribution is measured using a Malvern Mastersizer 2000 by Mie theory.

Storage Stability: The formulation should not exhibit visible phase separation after two weeks of storage, cycling the formulation between 60° C. and 5° C. every 2-3 days.

Results of the testing are shown in the following table.

|  | Formulation | | | | | |
|---|---|---|---|---|---|---|
| Test | 4A | | | 4B | | |
| Heat Stability | Maintained as solution | | | | | |
| Sonication Stability | | | | | | |
| Aqueous Dilution | Nanoemulsion formed | | | | | |
|  | D10 | D50 | D90 | D10 | D50 | D90 |
| Particle Size | 76 nm | 188 nm | 1130 nm | 79 nm | 196 nm | 2150 nm |
| Storage Stability | Maintained as solution | | | | | |

EXAMPLE 5

| Ingredient | % w/w |
|---|---|
| Progesterone (API) | 6.00 |
| Propylene Glycol Monocaprylate‡ (solubilizer) | 55.95 |
| Polyoxyl 35 Castor Oil* (emulsifier) | 35.00 |
| Hydroxypropyl Cellulose** (crystallization inhibitor) | 3.00 |
| dl-α-Tocopherol (antioxidant) | 0.05 |

‡e.g., CAPMUL ® PG-8, a product of Abitec Corp.
*e.g., KOLLIPHOR ® EL, a product of BASF
**e.g., KLUCEL ® EF, a product of Ashland Manufacturing Procedure:

1. At 55-60° C., propylene glycol monocaprylate and dl-α-tocopherol were combined; hydroxypropyl cellulose was slowly added with stirring until a solution was formed; progesterone was added and dissolved; and finally, Polyoxyl 35 castor oil was added and mixed well. Stirring of the solution was continued for 30 minutes after it was cooled to ambient temperature.

2. Quantities containing a desired amount of progesterone were encapsulated into hard gelatin capsules.

The formulation is tested for various properties, as follows:

Heat Stability: The formulation was heated to 60° C. and maintained for 30 minutes under stirring, then cooled to ambient temperature and maintained the stirring for 30 minutes. There should be no drug precipitation or separation of phases during the test.

Sonication Stability: The formulation was sonicated for 30 minutes, and there should be no visible phase changes.

Aqueous Dilution: The amount of formulation equivalent to 40 mg of progesterone was added to 250 mL of simulated gastric fluid and stirred slowly for 10-15 minutes. There should not be any visible phase separation and the formed dispersion should be transparent to translucent.

Particle Size: The dispersion (1-2 drops of the formulation in 160 mL of SGF) was maintained under continuous stirring and particle size distribution was measured using a Malvern Mastersizer 2000 by Mie theory.

Storage Stability: The formulation should not exhibit visible phase separation after two weeks of storage, cycling the formulation between 60° C. and 5° C. every 2-3 days.

Results of the testing are shown in the following table.

| Test | Result |
|---|---|
| Heat Stability | Maintained as solution |
| Sonication Stability | |
| Aqueous Dilution | Nanoemulsion formed |
| Particle Size | D10 = 74 nm<br>D50 = 114 nm<br>D90 = 195 nm |
| Storage Stability | Maintained as solution |

Pilot Fasting Bioavailability Study:

A randomized, open label, balanced, two treatment, two period, two sequence, single dose, two way crossover, bioavailability study of two capsules of progesterone capsules 40 mg (progesterone solution 6% w/w filled in hard gelatin capsules—test product) vs Prometrium® (progesterone capsules 200 mg—reference product) was performed in 12 healthy human volunteers. The $C_{max}/AUC_{0-t}$ and $AUC_{0-inf}$ of the test product is increased by ~7 fold, ~1.8 fold and ~1.6 fold, respectively over RLD.

|  | Least Square Mean | |
|---|---|---|
| Parameters | Test Product (Progesterone capsules) Dose normalized to 200 mg | Reference Product Prometrium ® (Progesterone capsules, 200 mg) |
| $C_{max}$ (pg/mL) | 13187.900 | 1912.491 |
| $AUC_{0-t}$ (pg · h/mL) | 11704.822 | 6523.494 |
| $AUC_{0-inf}$ (pg · h/mL) | 17205.885 | 10886.459 |

One embodiment of the pharmaceutical formulation, based on the above example, comprises progesterone, a solubilizer, an emulsifier, and a crystallization inhibitor. In further embodiments, the pharmaceutical formulation forms an emulsion when exposed to an aqueous environment, wherein a mean particle size (D50) of a droplet of the emulsion in said aqueous environment ranges from about 50 nm to about 200 nm.

The invention claimed is:

1. A pharmaceutical formulation comprising:
   a) abiraterone;
   b) propylene glycol monocaprylate; and
   c) an emulsifier.

2. The pharmaceutical formulation of claim 1, wherein the pharmaceutical formulation forms an emulsion when exposed to an aqueous environment; and further wherein a mean particle size (D50) of a droplet of the emulsion in said aqueous environment ranges from about 50 nm to about 800 nm.

3. The pharmaceutical formulation of claim 2, wherein the mean particle size (D50) ranges from about 50 nm to about 200 nm.

4. The pharmaceutical formulation of claim 1, wherein a difference in a solubility parameter of the active pharmaceutical ingredient and a solubility parameter of the non-aqueous solubilizer ranges from about 2 $(MPa)^{1/2}$ to about 7 $(MPa)^{1/2}$.

5. The pharmaceutical formulation of claim 1, wherein the emulsifier is selected from the group consisting of polyethoxylated oils, polysorbates, sorbitan esters of fatty acids, and combinations thereof.

6. The pharmaceutical formulation of claim 1, further comprising a crystallization inhibitor.

7. The pharmaceutical formulation of claim 6, wherein the crystallization inhibitor is selected from the group consisting of polyvinylpyrrolidones, cellulose ethers, and combinations thereof.

8. The pharmaceutical formulation of claim 1, further comprising a co-solvent.

9. The pharmaceutical formulation of claim 8, wherein the co-solvent is selected from the group consisting of propylene glycol, low molecular weight polyethylene glycols, triacetin, triethyl citrate, ethanol, glycofurol, and combinations thereof.

10. The pharmaceutical formulation of claim 1, wherein the formulation is in a dosage form comprising a capsule.

11. A method of forming a nanoemulsion in an aqueous fluid comprising, mixing the pharmaceutical formulation of claim 1 in an aqueous fluid.

* * * * *